(12) United States Patent
Fressinet et al.

(10) Patent No.: US 6,349,170 B1
(45) Date of Patent: Feb. 19, 2002

(54) CONTINUOUS RENAL REPLACEMENT THERAPY HEAT LOSS COMPENSATION

(75) Inventors: Jean-Louis Fressinet, St. Jean de Touslas; Alain Frugier, Tignieu, both of (FR); David B. Greene, Lakewood; James Little, Bailey, both of CO (US)

(73) Assignee: Gambro Inc., Lakewood, CO (US)

( * ) Notice: Subject to any disclaimer, the term of this patent is extended or adjusted under 35 U.S.C. 154(b) by 0 days.

(21) Appl. No.: 09/481,454

(22) Filed: Jan. 11, 2000

Related U.S. Application Data

(60) Provisional application No. 60/115,583, filed on Jan. 12, 1999.

(51) Int. Cl.[7] ................................................. A61F 7/00
(52) U.S. Cl. ........................ 392/470; 210/232; 604/5.04
(58) Field of Search ......................... 392/470; 604/4–6; 210/239, 240, 232

(56) References Cited

U.S. PATENT DOCUMENTS 5,211,849 A * 5/1993 Kitaevich .................. 604/5.04
6,047,108 A    4/2000 Sword et al. ............... 392/470

* cited by examiner

Primary Examiner—Tu Ba Hoang
Assistant Examiner—Thor Campbell
(74) Attorney, Agent, or Firm—Laura M. Butterfield; Edna M. O'Connor; Peter B. Scull

(57) ABSTRACT

An integrated CRRT method and apparatus incorporates steps and means for compensating for heat loss from blood in an extracorporeal circuit. A blood warmer is designed to engage and hold a disposable blood tube segment to transfer heat at a closely controlled temperature to blood flowing in the disposable blood tube segment. Another significant aspect of the present invention is a blood tube segment for engagement with the blood warmer is located in downstream of a dialyzer and upstream of a venous pressure monitor, an air bubble detector and a venous line clamp. The disposable blood tube segment may be selectively connected when heat loss compensation is required and left disconnected when heat loss compensation is not required.

9 Claims, 4 Drawing Sheets

ND REPLACEMENT
CONTINUOUS RENAL REPLACEMENT THERAPY HEAT LOSS COMPENSATION

RELATED APPLICATIONS

This application claims the priority of U.S. Provisional Patent Application No. 60/115,583 filed Jan. 12, 1999.

TECHNICAL FIELD

The invention relates to a method and apparatus for continuous renal replacement therapy. More particularly, this invention relates to a method and apparatus for compensating for extracorporeal heat loss from a patient undergoing continuous renal replacement therapy.

BACKGROUND

When a patient experiences renal failure, one of several extracorporeal blood treatment processes may be performed in order to replace the function of the failed kidneys. The processes include, without limitation, dialysis, ultrafiltration, hemofiltration, and hemodiafiltration, all of which, and similar processes, will be referred to herein collectively as "dialysis." Further "dialyzer" as used herein will be understood to mean a dialyzer, hemofilter or similar device. In the event of chronic, or permanent, kidney failure, also known as end stage renal disease, or ESRD, dialysis is usually performed at relatively high blood flow rates for around three or four hours, typically thrice per week. This type of periodic treatment challenges the patient's body, but is well tolerated by most ESRD patients as it offers them the opportunity for a relatively normal life.

Acute kidney failure, from which a patient may, in time, recover is often accompanied by other injuries or underlying disease which render the patient's body unable to withstand the rigors of periodic dialysis. These acute patients are usually treated at relatively lower blood flow rates and treated continuously. Also, very young patients are often unable to withstand the rigors of periodic dialysis and are often treated at low blood flow rate and/or continuously. This form of dialysis will be referred to herein as continuous renal replacement therapy or CRRT.

A method and apparatus for CRRT including equipment and disposable elements, is described in U.S. Pat. Nos. 5,394,732, 5,441,363 and 5,676,245 which are incorporated herein in their entirety by reference. Further, an apparatus for performing CRRT is sold by affiliates of the assignee of the present application under the tradename PRISMA™.

In dialysis some heat is generally lost to the environment from the blood circulating in the extracorporeal circuit, which, in time, results in loss of heat from the patient's body. In periodic treatment, the body's metabolic processes usually compensate for this heat loss and the patient's corporeal temperature is not significantly depressed. The continuous nature of CRRT increases the heat loss potential of the blood circulating in the extracorporeal circuit and the patient may, under certain circumstances, experience a depression of corporeal temperature.

It is, therefore, desirable, in some CRRT treatments, to compensate for heat loss from the patient's blood circulating extracorporeally. Fluid heaters have been used to heat either dialysate or infusate fluid. Typical blood flow rate in CRRT is approximately 120 ml/min while dialysate flow rate is typically 1 to 2 l/hr (16–33 ml/min). In order to transfer heat energy from the dialysate to the blood, it is necessary for the average temperature of the dialysate to be significantly higher than the average temperature of the blood. In the heat transfer zone between the dialysate and blood, which is typically a dialyzer or hemofilter, it is, under these circumstances, possible for the local blood temperature to be significantly higher than the average blood temperature. Average corporeal temperature in a healthy human patient is about 37° C. At local blood temperatures above 42° C., the blood may experience denaturing and flocculation of proteins and hemolysis.

Heating of the infusate fluid presents similar problems with regard to blood damage. Further, heat transfer from the infusate to the blood would be by direct mixing rather than across a dialyzer membrane further increasing the risk of blood damage. In addition, infusate flow is generally pumped, which means that it flows under negative pressure. Heating the infusate under negative pressure conditions can cause de-gassing of the infusate introducing air and other gas bubbles into the fluid flow. The resulting air may cause operational difficulties including the need to extract air from the CRRT system and excessive air embolism protection operation.

An affiliate of the assignee of the present invention produces a blood component separation centrifuge which includes an electric blood warmer under the trade name SPECTRATHERM™. A former affiliate of the assignee produces oxygenation systems for use in cardiopulmonary bypass surgery which incorporates fluid-to-fluid blood heat exchangers for heating and cooling blood under the tradenames, without limitation, CML™, VPCML™, OPTIMA™ and K+ARDIA™. Baxter Healthcare has suggested that a blood warmer may be used for CRRT in conjunction with its BMlla™ blood pump. It is against this background that the significant advances of the present invention were made.

SUMMARY OF THE INVENTION

It is an object of the present invention to provide an integrated CRRT method and apparatus which incorporates steps and means for compensating for heat loss from blood in an extracorporeal circuit. It is a further object of the invention to limit the local temperature experienced by the blood into levels which are not expected to damage the blood. It is a further object of the invention to minimize the generation of gasses which can cause operational problems in a CRRT method and apparatus. It is a still further object of the present invention to maintain adequate patient pressure and air embolism protection. It is a still further object of the present invention that the heat loss compensation method and apparatus be selectively usable. It is yet another object of the present invention to minimize the extracorporeal blood volume of a CRRT system when heat loss compensation is not required. Further objects of the present invention will be apparent from the detailed description of the preferred embodiment.

A significant aspect of the present invention for achieving at least one of the objects is a CRRT apparatus incorporating a blood warmer designed to engage and hold a disposable blood tube segment to transfer heat at a closely controlled temperature to blood flowing in the disposable blood tube segment. Another significant aspect of the present invention for achieving at least one of the objects is a blood tube segment for engagement with the blood warmer which is located in flow communication with and downstream of a dialyzer and upstream of one or combination of a venous pressure monitor, an air bubble detector and a venous line clamp. A further significant aspect of the present invention for achieving at least one of the objects is a dialysis disposable tubing set with which a disposable blood tube segment in the form of a blood line extension for engagement with the blood warmer may be selectively connected when heat loss compensation is required and left disconnected when heat loss compensation is not required.

Further significant aspects of the present invention will be apparent from the drawings, and from the detailed description of the preferred embodiment.

DETAILED DESCRIPTION OF THE PREFERRED EQUIPMENT

A presently preferred embodiment of the present invention will be described with reference to FIGS. 1–5. It will be understood by those skilled in the art that the present invention is not limited to the presently preferred embodiment but encompasses such variations as are apparent to one having skill in the art.

Figure 1:
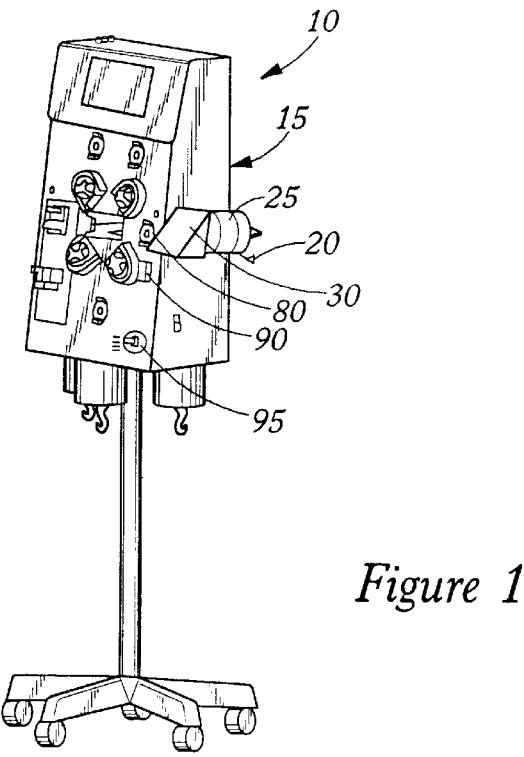
FIG. 1 is a perspective view of CRRT equipment incorporating a blood warmer in accordance with the present invention.

A continuous renal replacement therapy apparatus (CRRT) 10 in accordance with the present invention is illustrated in FIG. 1. The CRRT apparatus 10 comprises a CRRT monitor 15 and a blood warmer 20. The CRRT monitor 15 is preferably a PRISMA™ CRRT apparatus as sold by affiliates of the assignee of the present invention or the apparatus as generally described in U.S. Pat. Nos. 5,934,732, 5,441,363 and 5,676,245. The blood warmer 20 is preferably a Stihler model number 9662032 fluid warmer comprising a heat exchanger section 25 and a control section 30 and having an electric heat element internally disposed (not shown) and in thermal communication with the heat exchange section 25. The principles of operation of the blood warmer 20 are described in U.S. Pat. No. 4,709,135 which is incorporated herein in its entirety by reference. The electric heater of the blood warmer 20 is an ac heater rated at approximately 400 watts. The blood warmer 20 is mounted to one side of the CRRT monitor 15 by any suitable means, such as a bracket or handle mount.

Figure 2:
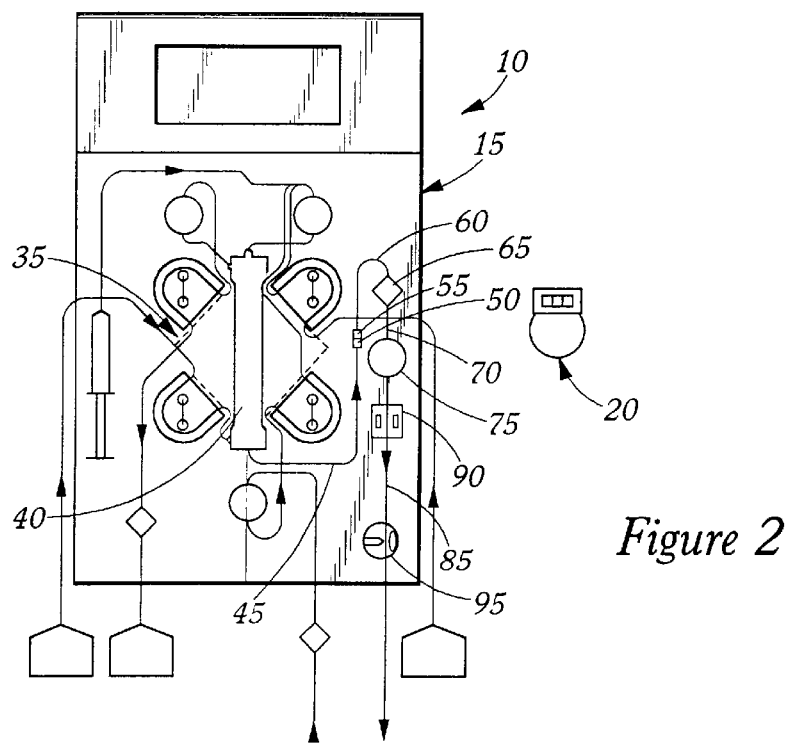
FIG. 2 is a diagrammatic view of the CRRT equipment of FIG. 1 with a CRRT dialysis disposable schematically illustrated as engaged therewith and configured to not compensate for heat loss in the extracorporeal circuit.

Referring to FIG. 2, a dialysis disposable tubing set 35 comprises an assembly of flexible medical tubes, peristaltic pump headers, a dialyzer, solutions, pressure pods, and sample access sites all assembled into a configuration as necessary to facilitate performing dialysis as that term is defined herein. The dialysis disposable tubing set 35 is mounted to the CRRT monitor 15 as illustrated in FIG. 2. A further description of a dialysis disposable tubing set 35 of the prior art, which may be adapted for use with the present invention, is included in U.S. Pat. Nos. 5,441,363 and 5,676,245. In pertinent part, the dialysis disposable tubing set 35 comprises a dialyzer 40 which, as stated above, may be a dialyzer or a hemofilter. A first venous line 45 is connected to the dialyzer and terminates in a first female luer connector 50. The first female luer connector 50 is connected to and in fluid communication with a first male luer connector 55. A second venous line 60 connects the first male luer connector 55 to a sample access site 65. A third venous line 70 interconnects the sample access site 65 with a pressure monitoring pod 75. The pressure monitoring pod 75 interconnects and cooperates with a venous pressure transducer 80 (FIG. 1) to transmit pressure occurring in the venous blood lines 70, 85 to the pressure transducer 80 which is a portion of the CRRT monitor 15. A fourth venous line 85 interconnects the pressure monitoring pod 75 with a return catheter (not shown), which is, in turn, connected to the patient to return treated blood to the patient. The fourth venous line 85 is threaded through an ultrasonic air bubble detector (UABD) 90, which serves as an air embolism protection detector, and, following the UABD 90, a venous clamp 95. The blood warmer 20 is illustrated in FIG. 2 as physically separate from the CRRT monitor 15 for clarity but it is, of course, physically mounted to the CRRT monitor 15 as described above.

The UABD 90 is advantageously an ultrasonic air bubble detector as described in U.S. Pat. No. 5,934,732. When it is not desired to compensate for heat loss in the extracorporeal blood circuit, the first female luer 50 is connected to, or remains connected to, the first male luer connector 55 as illustrated in FIG. 2. The UABD 90 and the venous clamp 95 interact with the fourth venous line 85 to detect air bubbles in the fourth venous line 85 and, upon detection of air bubbles in the fourth venous line 85 by the UABD 90, to close the venous clamp 95 in order to protect the patient from infusion of air bubbles or an air embolism, which can have a deleterious effect on the patient.

Figure 3:
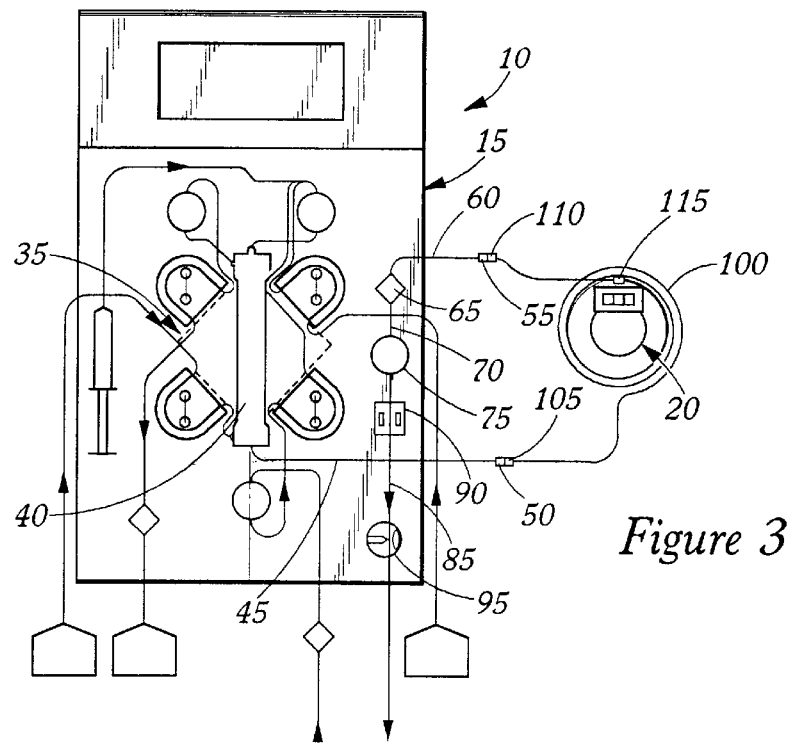
FIG. 3 is a diagrammatic view of the CRRT system of FIG. 1 with a dialysis disposable schematically illustrated as engaged therewith and configured to compensate for heat loss in the extracorporeal circuit.

FIG. 3 illustrates the CRRT monitor 15 and blood warmer 20 of the present invention configured to compensate for heat loss in the extracorporeal blood circuit. A venous extension line 100 has a second male luer connector 105 at a first end and a second female luer connector 110 at a second end of the extension line 100. The extension line 100 comprises flexible, medical tubing as is well known in the art. In the preferred embodiment the extension line 100 comprises approximately 425 centimeters of soft PVC medical tubing having an outside diameter of 6.8 millimeters and an inside diameter of 4.8 millimeters. Sterility caps (not shown) are provided over the luer connectors 105, 110 to maintain sterility of the extension line 100 prior to use. An alignment marker tape 115 is provided near the end of the extension line 100 which is terminated in the second female luer connector 110. The extension line 100 is installed on the blood warmer 20 as described below. The extension line 100 is engaged helically on the heat exchanger section surface 25 (FIG. 1) of the blood warmer 20. The first female luer connector 50 is disconnected from the first male luer connector 55, (FIG. 2), and the first female luer connector 50 is connected to the second male luer connector 105 and the first male luer connector 55 is connected to the second female luer connector 110 (FIG. 3). Accordingly, the blood flowing in the first, second, third and fourth venous lines 45, 60, 70, 85 also flows in the tubing extension 100 and further flows through the extension line 100 prior to encountering the sample access site 65, the pressure pod 75, the UABD 90 and the venous clamp 95. Thus any gasses generated in the extension tubing as a consequence of heat transferred from the blood warmer 20 will be detected by the UABD 90 and actuate the venous clamp 95 to protect the patient from infusion of air. In addition, most, if not all, of such gasses generated in the extension line 100 will be collected in the access site 65 where they can be removed from the access site 65 using a syringe and conventional techniques. Further, because the blood warmer 20 and extension line 100 are located in the circuit upstream of the pressure pod 75, the pressure pod 75 will continue to be indicative of the true venous pressure at the patient and will be unaffected by the pressure loss in the extension line 100.

Figure 4:
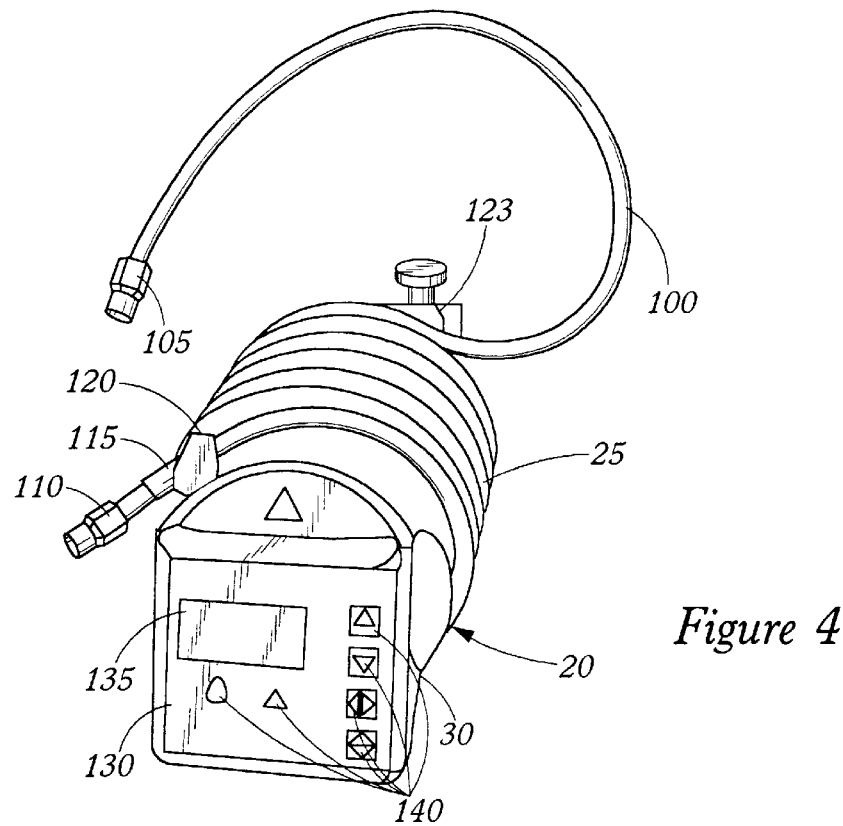
FIG. 4 is a perspective view of the blood warmer of FIG. 1 with a blood line extension installed thereon.
Figure 5:
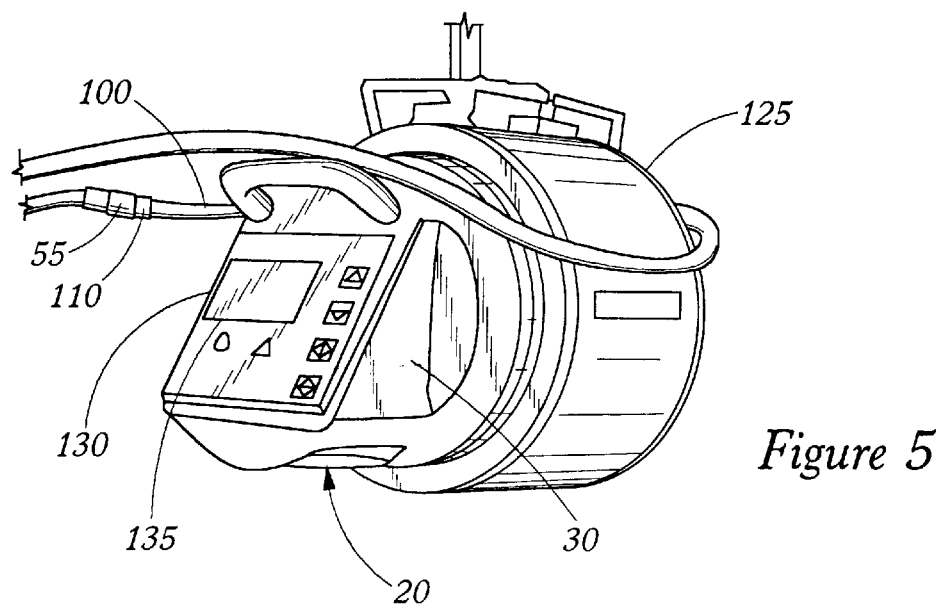
FIG. 5 is a perspective view of the blood warmer of FIG. 4 with a thermal sleeve installed over the blood line extension.

FIGS. 4 and 5 illustrate loading the extension line 100 into the blood warmer 20. The alignment marker tape 115 is placed under a front tubing clip, 120, of the blood warmer 20. The heat exchanger section 25 of the blood warmer 20 comprises an external cylindrical surface having a helical groove (not shown) running from a front end of the heat exchanger section 25 to the rear end. The helical groove has a generally semicircular cross section which mates with and accepts tubing of the outside diameter of the extension line 100. The extension line 100 is wound helically into the helical slot from the front end of the heat exchanger section 25 to the rear end and secured under a rear tubing clip 123. In the preferred embodiment, the extension line 100 makes nine helical turns about the heat exchanger section 25. Once the extension line 100 has been installed in the helical groove, a clam-shell thermal sleeve 125 is installed over the heat exchange section to hold the extension line 100 in place and to improve the heat transfer characteristics from the heat exchange section 25 to the extension line 100.

In the preferred embodiment, a bracket 150 which mounts the blood warmer 20 to the CRRT monitor 15 is a swivel mount which permits swiveling the blood warmer 20 away from the CRRT monitor 15 for installation of the extension line 100 and clam-shell thermal sleeve 125 and swiveling the blood warmer 20 back to a more convenient operating and connection position once the extension line 100 has been installed.

Figure 6:
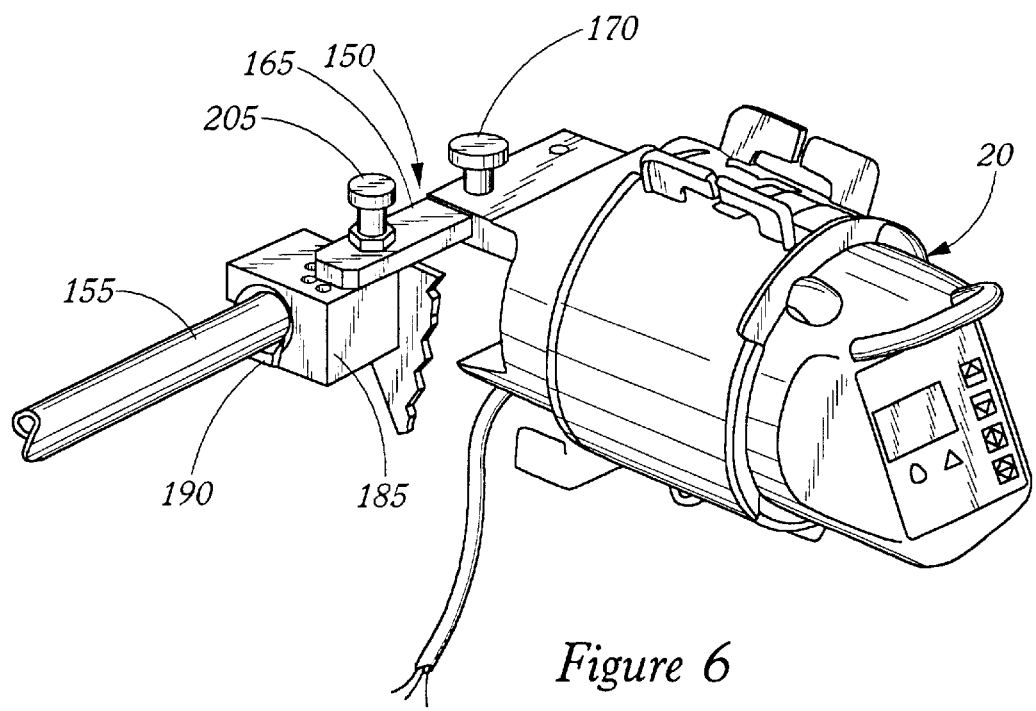
FIG. 6 is a perspective front view of the blood warmer of FIGS. 4 and 5 installed on the CRRT equipment by means of a mounting bracket.
Figure 7:
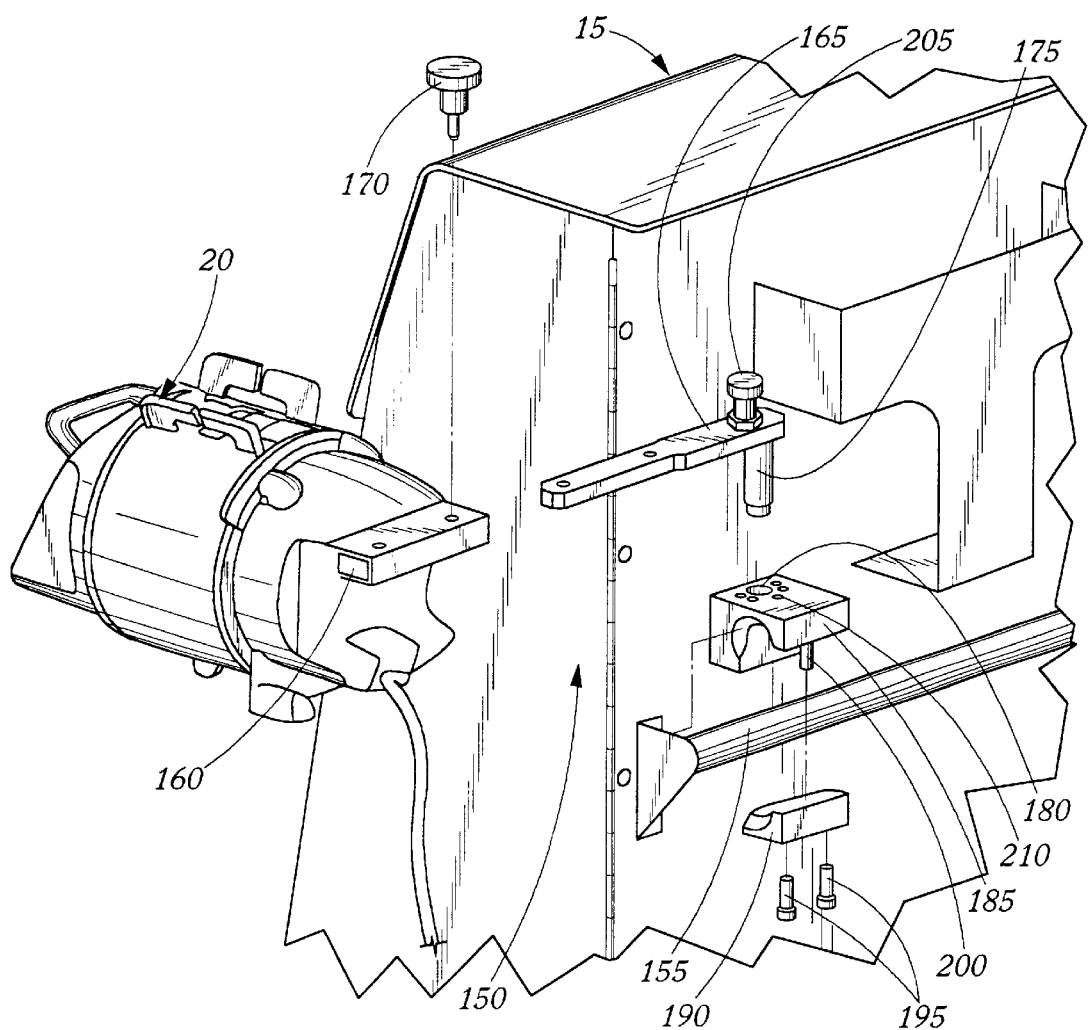
FIG. 7 is a perspective rear view of the CRRT equipment including an exploded view of the mounting bracket of FIG. 6.

As illustrated in FIGS. 6 and 7 the mounting bracket 150 attaches to a tubular handle 155 affixed to the rear of the CRRT monitor 15 to hold the blood warmer 20 in place. A horizontally oriented recess 160 in the rear of the blood warmer 20 receives a mounting arm 165 of the mounting bracket 150. A retainer screw 170 secures and retains the mounting arm 165 in the recess 160. The mounting arm 165 is affixed perpendicularly to a cylindrical pivot pin 175 which fits slidingly and rotatably into a vertically oriented pivot hole 180 in a clamp block 185. The clamp block 185 inter-fits with and cooperates with a clamp 190 to secure the clamp block 185 and clamp 190 around the tubular handle 155, oriented so that the mounting arm 165 is above the clamp block 185 and extending horizontally, and with the pivot pin 175 oriented vertically. The clamp 190 is secured to the clamp block 185 by two screws 195 and an alignment pin 200.

Thus attached to the CRRT monitor 15 the mounting arm 165 and blood warmer 20 can be swiveled in a horizontal plane. A spring knob 205 is affixed to, and passes through, the mounting arm 165 and cooperates with a plurality of holes 210 in a top surface of the clamp block 185 to selectively retain the mounting arm 165 and blood warmer 20 in one of a plurality of angular positions in the horizontal plane, including the position for installation of the extension line 100 and thermal sleeve 125 and the operating and connection position.

The control portion 30 of the blood warmer 20 has a microprocessor to operate the electric heating element and to control the temperature of the heat exchanger section 25. A control panel 130 on the control portion 30 has a visual display panel 135 and a plurality of input and indicating devices 140. The control portion 30 controls the temperature at the heat transfer surface of the heat exchanger section 25 of the blood warmer 20 to an operator selected set point value. The operator may select a set point value 37° C., 39° C., or 41° C. By establishing the highest allowable set point value for the surface temperature of the heat exchanger section 25 of the blood warmer 20 at 41° C., the maximum desirable warmed blood temperature of 42° C. will not be exceeded in normal operation of the blood warmer 20. If the temperature of the surface of the heat exchanger section 25 exceeds 42.5° C. the blood warmer 20 over temperature indicator on the control panel 130 will be activated.

The invention has been described by reference to a preferred embodiment, it being understood that the invention is not limited to the described embodiment. The present invention is defined by the spirit and scope of the following claims.

What is claimed is:

1. A continuous renal replacement therapy system comprising:
   a continuous renal replacement therapy monitor having a venous pressure transducer, a detector for protecting against air embolism, and a venous line clamp;
   a blood warmer capable of being attached to the continuous renal replacement therapy monitor;
   an extension line adapted to be received by and cooperate with the blood warmer;
   the system further comprising a disposable blood tubing set adapted for engagement to the continuous renal replacement therapy monitor comprising;
   a first venous line;
   a second venous line;
   a separable connector pair intermediate the first and second venous line capable of being connected to the extension line for cooperation with the blood warmer;
   a third venous line;
   a sample access site intermediate the second venous line and the third venous line;
   a fourth venous line; and
   a venous pressure pod intermediate the third and fourth venous lines;
   wherein said fourth venous line is adapted to be received by and cooperate with the detector for protecting against air embolism, and with the venous line clamp.

2. The extension line of claim 1 further comprising:
   a first end and a second end, each end having one half of a connector pair adapted to interconnect with the halves of the separable connector pair of the disposable tubing set when separated, whereby the extension line is intermediate the first and second venous lines when attached to the blood warmer.

3. A continuous renal replacement therapy system comprising:
   a continuous renal replacement therapy monitor having a venous pressure transducer, a detector for protecting against air embolism, and a venous line clamp;
   a blood warmer capable of being attached to the continuous renal replacement therapy monitor; and a disposable tubing set adapted for engagement with the continuous renal replacement therapy monitor, comprising:
  a first venous line;
  a third venous line;
  a sample access site intermediate the first venous line and the third venous line;
  a fourth venous line; and
  a venous pressure pod intermediate the third and fourth venous lines; wherein
    said fourth venous line is adapted to be received by and cooperate with the detector for protecting against air embolism, and with the venous line clamp; and
    said first venous line is adapted to be received by and cooperate with the blood warmer.

4. A method of continuous renal replacement therapy comprising:
  passing treated blood through a blood warmer prior to passing it though any one or more of:
    a sample access site;
    a venous pressure monitor;
    an air embolism protection detector; and
    a venous clamp.

5. The method claim 4 wherein the venous blood is passed through the blood warmer prior to passing it through:
  the air embolism protection detector; and
  the venous clamp.

6. The method claim 5 wherein the venous blood is further passed through the blood warmer prior to passing it through the sample access site.

7. The method of claim 6 wherein the venous blood is further passed through the blood warmer prior to passing it through the venous pressure monitor.

8. The method of claim 5 wherein the venous blood is further passed through the blood warmer prior to passing it through the venous pressure monitor.

9. The method of claim 4 wherein:
  the treated blood is passed through the sample access site after it is passed through the blood warmer;
  the treated blood is passed through the venous pressure monitor after it is passed through the sample access site;
  the treated blood is passed through the air embolism protection detector after it is passed through the venous pressure monitor; and
  the treated blood is passed through the venous clamp after it is passed through the air embolism protection detector.

* * * * *